United States Patent [19]

Lazerson

[11] Patent Number: 5,342,377
[45] Date of Patent: Aug. 30, 1994

[54] ROTATING BLADE CAPSULOTOMY INSTRUMENT AND METHOD OF PERFORMING A CAPSULOTOMY

[76] Inventor: Howard E. Lazerson, 935 Glenhaven Dr., Pacific Palisades, Calif. 90277

[21] Appl. No.: 52,795

[22] Filed: Apr. 23, 1993

Related U.S. Application Data

[63] Continuation-in-part of Ser. No. 992,610, Dec. 18, 1992, abandoned.

[51] Int. Cl.⁵ .............................................. A61B 17/32
[52] U.S. Cl. .................................. 606/166; 606/170; 30/321
[58] Field of Search ............... 606/107, 166, 167, 170, 606/171, 180; 30/317, 321

[56] References Cited

U.S. PATENT DOCUMENTS

| | | | |
|---|---|---|---|
| 4,657,012 | 4/1987 | Burgin | 606/167 |
| 4,708,138 | 11/1987 | Pazandak | 606/107 |
| 4,766,896 | 8/1988 | Pao | 606/170 |
| 4,885,004 | 12/1989 | Pao | 604/22 |
| 5,156,607 | 10/1992 | Kansas | 606/170 |
| 5,203,865 | 4/1993 | Siepser | 606/166 |
| 5,217,476 | 6/1993 | Wishinsky | 606/107 |
| 5,222,960 | 6/1993 | Poley | 606/107 |

FOREIGN PATENT DOCUMENTS 165657 12/1985 European Pat. Off. ............ 606/166

*Primary Examiner*—Ralph Lewis
*Attorney, Agent, or Firm*—Beehler & Pavitt

[57] ABSTRACT

An instrument and method for performing a capsulotomy where the instrument is in the form of a tubular probe through which irrigation fluid may be passed, the end of the probe carrying a thin blade pivotable about an axis transverse to the axis of the tubular probe, the blade being disposed eccentrically with reference to the axis, with its major trailing cutting edge located toward the rear of the blade and at a greater distance from the axis than the leading end of the blade so that, when the leading end of the blade is applied to cut the anterior wall of the capsule, the cutting is completed by the swiveling of the blade about the axis to follow the movement of the leading end. The method involves the use of this blade to perform a circular cut in the capsule wall through which the cataract may be drawn out.

18 Claims, 4 Drawing Sheets

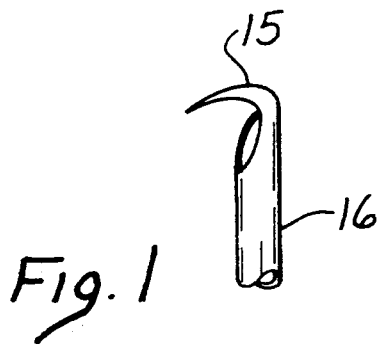
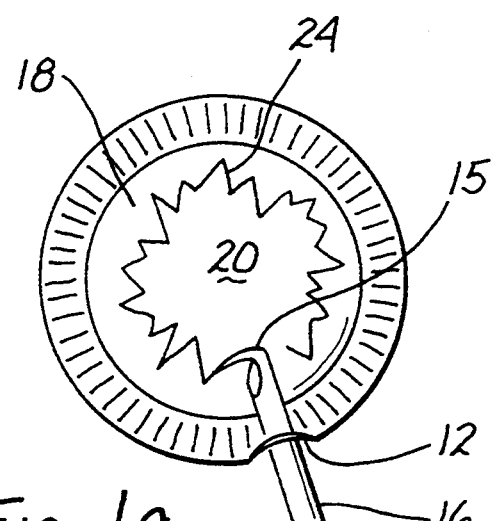
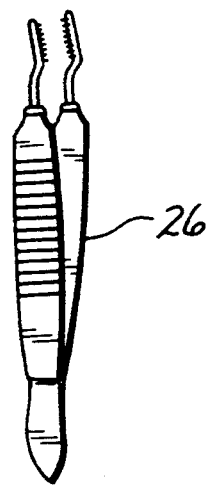
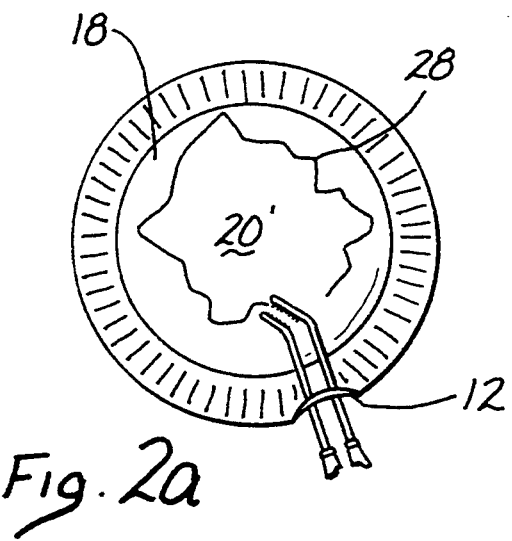
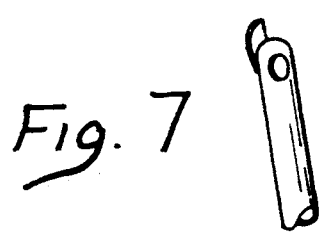
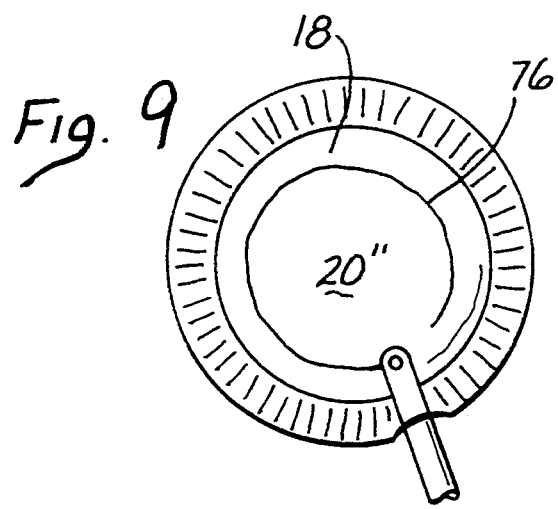

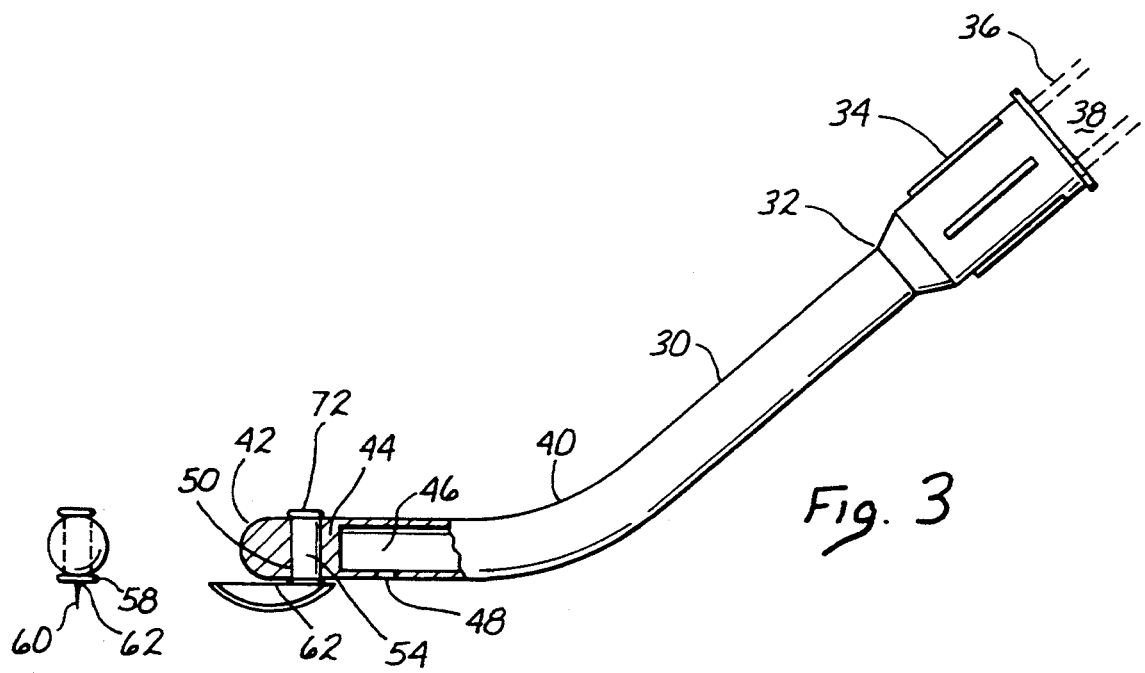
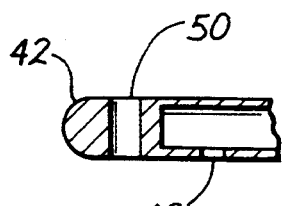
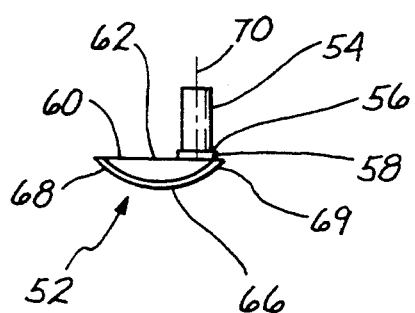

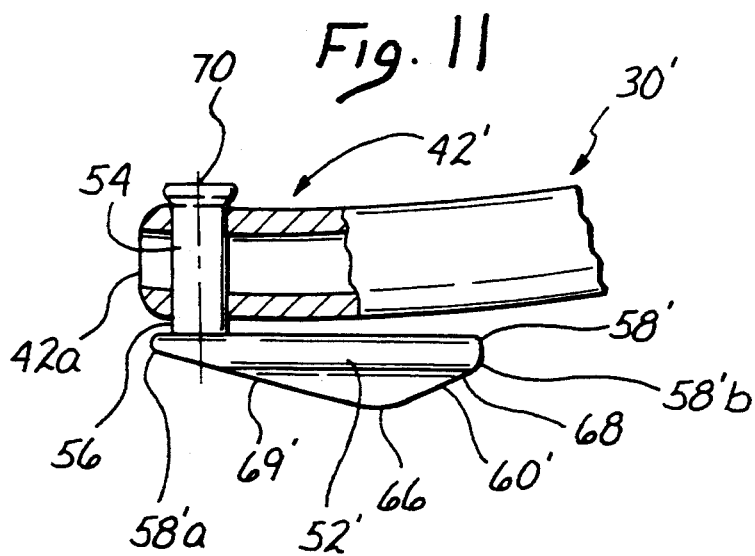
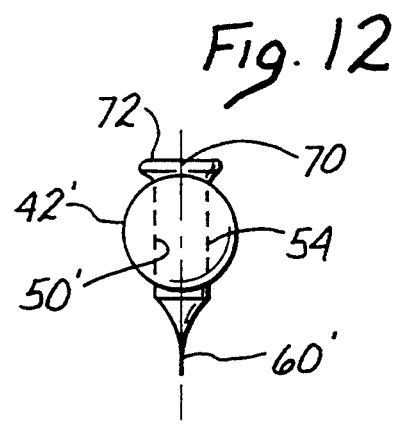
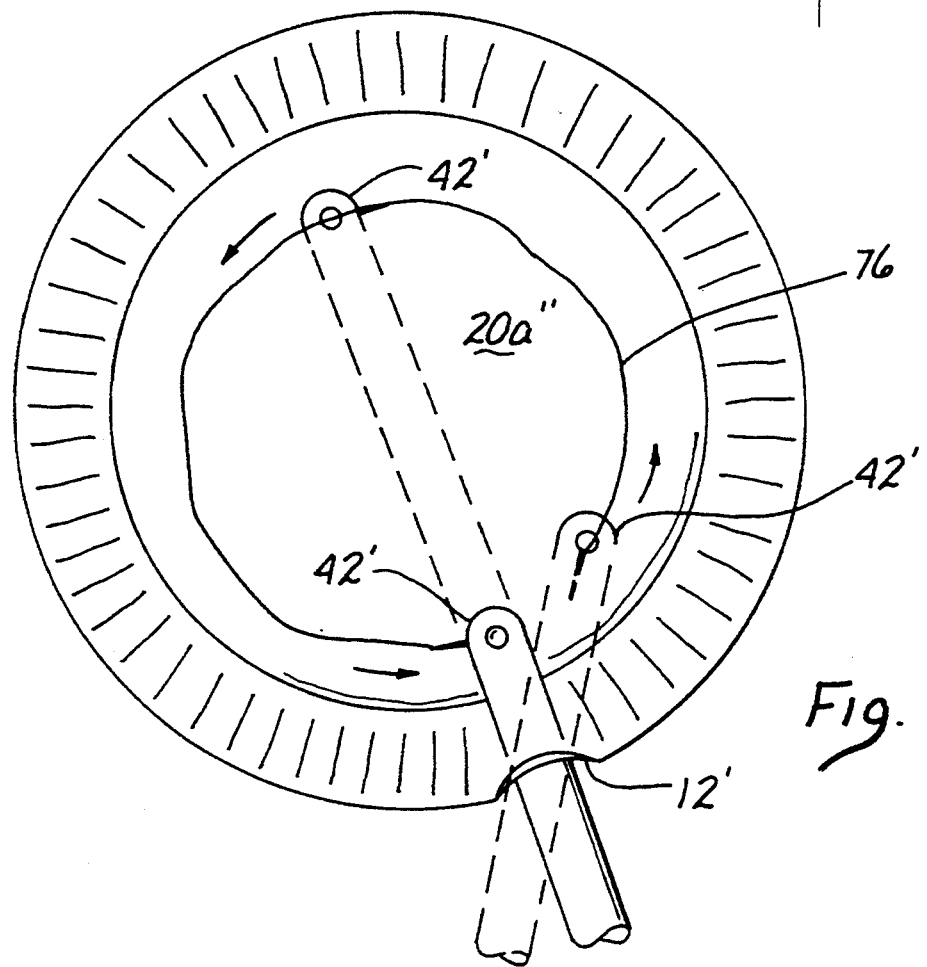

ial instruments and, particularly, to instruments which
ROTATING BLADE CAPSULOTOMY INSTRUMENT AND METHOD OF PERFORMING A CAPSULOTOMY This is a continuation-in-part of U.S. application Ser. No.: 07/992,610 filed Dec. 18, 1992 and now abandoned.

FIELD OF THE INVENTION

This invention relates generally to the field of surgical instruments and, particularly, to instruments which are used in eye surgery for the purpose of accomplishing capsulotomies, and to a limited method of performing such eye surgery.

BACKGROUND OF THE INVENTION

Cataracts form within the capsule of the human eye. Removal of the cataract may be accomplished by making an opening, preferably generally circular in configuration, in the anterior capsule wall (a capsulotomy) through which a thin suction element may be inserted to draw out the cataract.

Heretofore, instruments which have been made available to, and used by, eye surgeons for the purpose of making the necessary opening in the wall of the anterior capsule of the eye have included bent needles, cystotomes, forceps and small scissors. The basic problem with each of these prior art instruments, when used for making the required opening in the anterior capsule wall, is that each tends to tear the capsule wall thereby producing an opening defined by jagged edges in the wall. Not only is effecting the required opening in the anterior capsule wall which is made by prior art devices time consuming, but it is difficult for the surgeon to make an optimum sized and shaped opening. This latter difficulty is an inevitable result of the ripping or tearing effected by prior art instruments. Moreover, where the edges of the opening are jagged or may have wall strips or portions projecting into the wall opening which has been made, these can interfere with the suction process which follows the removal of the cataract.

In any event, performing a proper and adequate capsulotomy with any of the prior art instruments has required a very high degree of skill and experience on the part of the eye surgeon, and even then may sometimes produce an undesired shape and/or size of the wall opening.

SUMMARY OF THE INVENTION

The present invention enables the eye surgeon to avoid the problems created by the inherent tearing action of prior art instruments by providing a small elongated arcuate knife having a rectilinear back side and an oppositely extending arcuate cutting side. The back side of the blade is mounted perpendicularly on a small supporting rigid base, which could be in the form of a narrow plate or plate-like portion, and may extend within the full length of the back side of the blade, and for only part of such length. The blade and base preferably may be integrally formed as a single forged piece. One end of the blade constitutes the leading end; the opposite end the trailing end. For a most effective instrument, the apex of the blade arc should be closer to the trailing end, and the blade edge at the apex and on the both sides of the arch adjacent its apex should be thin and highly sharpened. The blade is rotatingly mounted on the rounded end of a hollow probe-like member by means of an axle extending perpendicularly from the back side of the base of the blade. The axle is passed through, and secured against withdrawal from, but may rotate within, a transverse orifice adjacent the rounded end of the probe-like member.

The supporting blade base should be eccentrically disposed with reference to the axle and may extend either partially or wholly below the back side of the blade so that the distance between the leading end of the blade and the axis of the axle is substantially less than the distance between such axis and the trailing end of the blade. Thereby, when the leading edge of the blade is pressed into the anterior wall of the eye capsule and moved in a circular course to effect a cutting, the blade will be castored or swivel about the axis of the axle to track the path cut by the blade's leading edge and thereby provide for a clean cut of the configuration (generally circular) desired by the surgeon to create an opening of the optimum size and configuration for accomplishing removal of the cataract.

The opposite end of the probe may be coupled as an attachment to a handle device to be grasped by the surgeon for accomplishing the capsulotomy. Desirably, the probe should be hollowed at least to a point near the transverse opening supporting the blade axle. If the end of the probe should be closed, a small lateral port should be provided in the hollowed out portion of the probe close to the end of such portion through which port irrigating fluid may be passed through the probe. Alternatively, if the end of the probe should be open, the irrigating fluid may be simply dispensed through such end.

Because a small thin sharp blade is employed and castored in the manner above described, no tearing of the capsule wall occurs. The eye surgeon, thus, may avoid producing jagged or irregular edges defining the opening made in the capsule wall. Moreover, the surgeon will have complete control over the size and configuration of the opening which he wishes to effect to accomplish the cataract removal. With considerably less practice and experience, a surgeon may, thus, properly accomplish cataract surgery.

Lastly, while the instrument of the present invention requires skill and precision in its fabrication, it may be produced at a reasonable cost so that it may be economically disposed of after a single use. Although it would be possible to reuse the blade after having it autoclaved, such use is not considered desirable since autoclaving may have an adverse effect upon the blade.

DESCRIPTION OF THE DRAWINGS

In the accompanying drawings,

FIG. 1 is a side elevation greatly enlarged of the head of a prior art instrument known as a cystotome.

FIG. 1a is an enlarged plan view of the manner in which an opening is made in the wall of the anterior capsule of a cystotome.

FIG. 2 is an enlarged perspective view of a capsulotomy forceps.

FIG. 2a is an enlarged plan view of the opening in the anterior wall of a lens capsule made by the forceps of FIG. 2.

FIG. 3 is an enlarged side elevation partly broken away of a probe to which a pivoting blade has been attached in accordance with the present invention.

FIG. 3a is an end view looking in from the left side of the lower end of FIG. 3.

FIG. 4 is a side elevation of the blade and axle mount shown in FIG. 3.

FIG. 5 is a view similar to the lower portion of FIG. 1 showing the axle supported blade removed from the probe end.

FIG. 7 is a perspective view in reduced size of a probe end on which is mounted a rotating blade of the type shown in FIGS. 3, 3a, 4 and 5.

FIG. 9 is a plan view of a lens capsule illustrating the manner in which the rotatable knife of the present invention would be moved to complete cutting the desired circular opening.

FIG. 11 is an enlarged side elevation, partly in section, of the preferred form of the probe and blade element of the present invention.

FIG. 12 is an end view of the probe and blade element looking from the left side of FIG. 11.

FIG. 13 is an enlarged plan view similar to FIGS. 9 and 10 illustrating the movement of the probe and blade in effecting a capsulotomy.

DESCRIPTION OF THE PREFERRED EMBODIMENT

Figure 6:
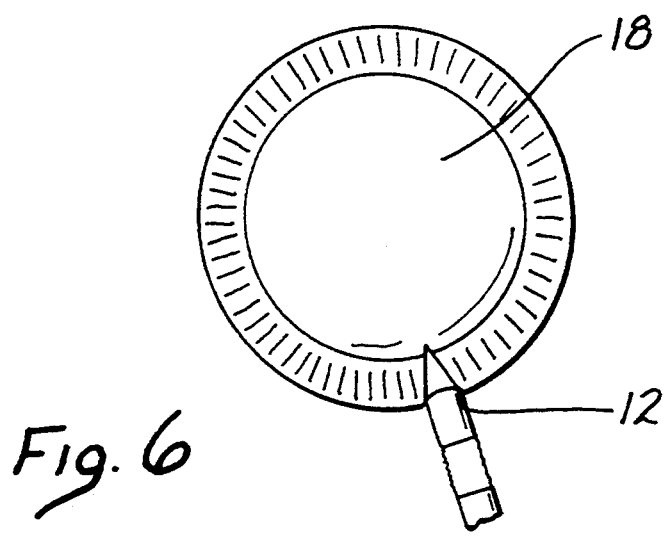
FIG. 6 is a plan view of a lens capsule as it would be approached by a sharp knife making the initial incision into the eye for insertion of an instrument to accomplish a capsulotomy.

For an understanding of the operation and utility of the present invention, it is deemed best first to explain how a capsulotomy is performed by presently available instruments.

Referring to FIG. 1a, after a small incision 12 is made into the eye, the head 15 of an instrument, such as a cystotome 16, is inserted and brought into contact with anterior capsule wall 18 to accomplish the capsulotomy. When a cystotome 16 is employed, after it is inserted through the incision 12, its 22 pointed head 15 is moved against the anterior capsule wall 18 to produce an opening 20, but this is done by picking and tearing through the wall to produce such opening 20 defined by a series of jagged edges 24, as shown in FIG. 1a.

Similarly, when a prior art forceps 26 of FIG. 2 is employed in the manner shown in FIG. 2a to produce the opening 20', again the opening 20' will be found to be defined by irregular jagged edges 28.

The configurations of the edges 24 and 28 defining the openings 20 and 20', respectively, necessarily results from the manner in which the cystotome and the forceps 26 must be employed to produce their respective openings in the anterior capsule wall 18, i.e. by picking and tearing. Not only is it difficult for the surgeon to make the desired opening 20, 20', by such picking and tearing action, but it is difficult to make the opening of the most desirable configuration and optimum size for accomplishing the remainder of the operation.

With the foregoing background information, the operation and utility of the instrument of the present invention may now be explained and fully understood. What is provided as shown in FIGS. 3, 3a, 4, 5 and 7, is a thin, tubular probe 30, one end of which 32 includes a base 34 adapted for coupling to some type of handle means 36 (shown in dotted lines) which may include a passage 38 through which irrigating fluid may be supplied. The probe 30 may be bent at 40 toward its forward end 42. The latter may comprise a closed solid head 44 which terminates the passage 46 in the hollow tube 30. The passage 46 may extend to the opposite end 32 for communication with the source of fluid 38 in the handle means 36. A small lateral port 48 may be provided near the solid head portion 44 of the probe end 42 through which port 48, irrigation fluid may be extended. In addition, a transverse orifice is drilled or otherwise formed to extend through the solid head portion 44 of the end 42' as best shown in FIGS. 3 and 5. Alternatively, the forward end 42' of the probe 30' may be open, as shown in FIG. 11, in which case the irrigation fluid may pass through the opening 42a and no lateral port 48 would be required for irrigation purposes.

A cutting element 52, as best shown in FIGS. 4, 11 and 12, is provided for rotatable attachment to the probe end 42 or 42'. This cutting element may comprise a cylindrical axle 54, secured at its lower end 56 to a narrow rigid supporting base portion 58 (or 58' in FIG. 11). Extending vertically downwardly from the lower side of the base portion 58 (or 58') is a thin arcuate blade portion 60 or 60', as best shown in FIGS. 3a, 4, 11 and 12.

In the embodiments of FIGS. 3, 3a and 4, the blade portion may comprise a back side 62, at least a portion of which is secured centrally to separate base portion or plate 58. The supporting base portion or plate 58 may extend the full length of the back side 62 of the blade 60, or if the blade itself may be made rigid enough, the base portion 58 could extend only part way along the back side of the blade 60. In the embodiment shown in FIGS. 11 and 12, the base portion 58' and blade 60' are forged, or otherwise formed, as a unitary piece so that the base portion 58' simply tapers down to the sharpened cutting edge 64. The latter desirably should be formed asymmetrically so that the zenith 66 of the blade arch lies closer to sharpened blade end 68 (the trailing end) than to the opposite end 69 (the leading end). This latter blade configuration has been found to be most desirable to accomplish a capsulotomy in the manner hereinafter explained, although other blade configurations may also be found to be acceptable.

It is also a feature of the present invention to provide for the leading end 58' of the base portion 58' to be disposed closer to the axle 54 than the trailing end 58'b. Thereby, cutting element 52 is disposed eccentrically with respect to the axis 70 of the cylindrical axle element 54.

The cutter element 52 (or 52') is mounted on the end 42 (or 42') of the probe 30 (or 30') by inserting the cylindrical axle 54 in the transverse orifice 50 or (50') and peening the upper end of the axle 54 at 72, or otherwise securing the axle 54 in the transverse orifice 50 (or 50'), to prevent the withdrawal from the latter while permitting the axle and the blade element 52 (or 52') mounted thereon to rotate or swivel about the probe end 42 (or 42').

Figure 8:
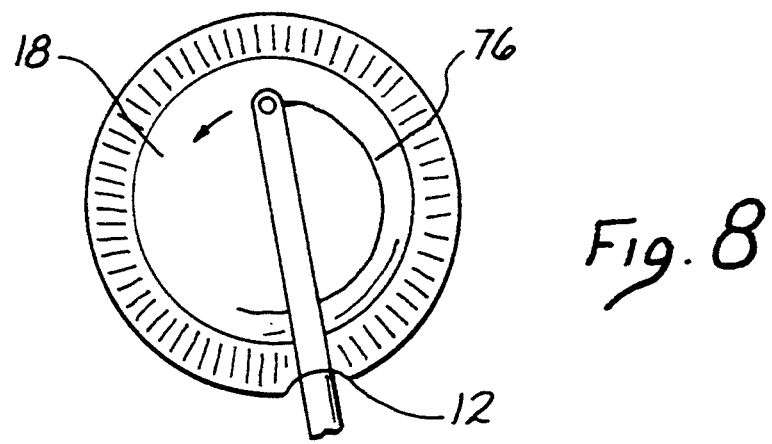
FIG. 8 is a plan view of an anterior capsule showing the initial movement of an instrument of the present invention to make the desired opening.
Figure 10:
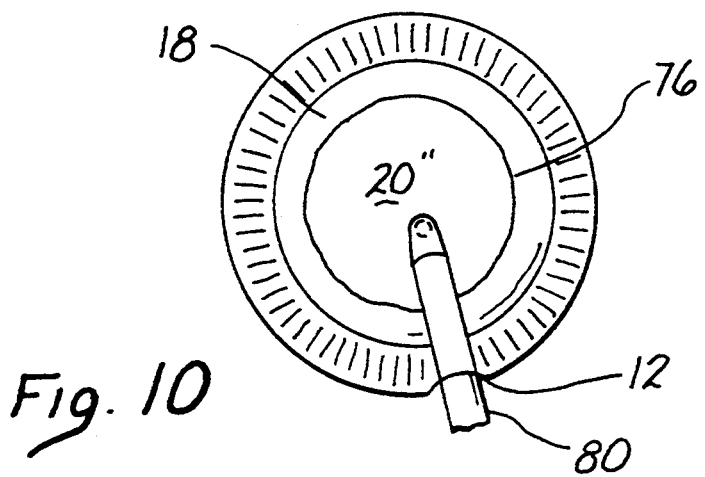
FIG. 10 is a plan view illustrating the manner in which a vacuum instrument may be inserted through the opening made in the anterior wall of the capsule, to draw out the cataract.

In use, the instrument of the present invention is inserted through the incision 12 and its end 42 (or 42') is then moved in a circular manner shown in FIGS. 8 and 9. With this movement, it will be found that the end 64 of the blade 60, which end is secured to the plate 58 will commence cutting a circular opening 76 in the capsule wall 18 in the manner shown in FIGS. 8, 9 and 13. As the blade 60 (FIG. 4) or 69 (FIG. 11) is moved to initiate cutting, the arched portion 66 will complete the cutting through the anterior wall 18 in the desired circular path 76. Such circular path 76 will be cut by the arcuate blade 60 (or 60') since the blade will pivot or rotate about the axis 70 of the axle 54 turning in the transverse opening 50 (or 50'), with the opposite or trailing end 68 of the blade 60 ( FIG. 4), or the trailing end 60' of the blade 60' (FIG. 11) being swung around to track the movement of the leading end 69 (or (69') to accomplish a clean cutting of the circular opening 76 as shown in FIGS. 8, 9 and 13, and, finally, in FIGS. 10 and 13. At this point then, as shown in FIG. 10, a suction instrument 80 may be inserted into the circular opening 20" (or 20a") which has been effected by the movement of the pivoting arcuate blade 60 (or 60'), hereinabove explained.

The preferred embodiment of the probe and cutter element combination is that illustrated in, and described with reference to, FIGS. 11, 12 and 13.

It will be found that the instrument of the present 15 invention will enable the surgeon to make an effective circular opening of whatever size he desires with clean, regular, circular edges in the place of the jagged edges which have necessarily resulted from the use of the prior art instruments, as shown in FIGS. 1a and 2a. The instrument of the present invention, and the method of performing a capsulotomy therewith, thus, may be expected to shortly replace all prior art instruments and methods for performing capsulotomies.

I claim:

1. An instrument for performing a capsulotomy whereby an opening is cut into the wall of the anterior capsule of a human eye, said instrument comprising:
   handle means;
   a probe, said probe being formed as a thin rigid elongated cylindrical element having a first base end and a second closed end, said first base end being adapted for coupling to the handle means and said probe being transversely orificed perpendicularly to its axis, and inwardly of, but adjacent to, the second closed end of the probe;
   an axle rotatably mounted on the second closed end of said element through said transverse orifice and co-axially with said orifice, said axle having a first end and a second end, said first end being secured against withdrawal through the orifice, and said second axle end projecting from said orifice,
   a rotatable cutter element, said cutter element comprising a thin, downwardly projecting rigid arcuate sharp blade, said blade having a base portion with a first leading end and a second trailing end, and a cutting edge section, said blade cutting edge section being convexly curved away from said base portion for a full distance between said first and second ends of said base portion, and said base portion being secured to the second projecting end of said axle along a portion of said base portion closer to the first leading end of the blade than to its second trailing end, whereby the blade is eccentrically mounted so that upon application of the leading edge of the blade to a surface to be cut in a predetermined path, the blade rotates about the axis of the axle to cause the trailing end of the blade to follow said predetermined path.

2. The instrument as described in claim 1 wherein the second closed end of the cylindrical element is rounded.

3. The instrument as described in claim 1, wherein the cylindrical element is bent at an angle inwardly of its second closed end.

4. The instrument as described in claim 1, wherein cylindrical element is hollow to a point adjacent the transverse orifice, and an opening is provided in the hollowed portion of the element in the vicinity of the transverse orifice to enable irrigating fluid to be passed through the probe and out of the opening.

5. An instrument for performing a capsulotomy whereby an opening is cut into the wall of the anterior capsule of a human eye, said instrument comprising:
   handle means;
   a probe, said probe being formed as a thin rigid cylindrical element having a first base end and a second rounded end, said first base end being adapted for coupling to the handle means and said probe being transversely orificed perpendicularly to its axis and inwardly of, but adjacent to, its second rounded end; and
   a narrow, flat support plate, said plate being of a predetermined length and having an upper side and a lower side;
   an axle, said axle projecting perpendicularly from and secured to the upper side of said plate adjacent one end thereof;
   an arcuate blade having first and second opposing ends being secured to, and extending from and below a central portion of the lower side of said plate, said first end of said blade being disposed at a greater distance from an axis of said axle projected through said plate than said second end of said blade, said blade having a cutting edge section extending between said first and a second ends and arched convexly downwardly with respect to said plate at all areas thereof;
   said cutter element being rotatably mounted adjacent said second rounded end of the probe by insertion of said axle through said transverse orifice, and said axle being secured from withdrawal from said orifice;
   whereby, when said second end of said probe is advanced into close proximity with the anterior eye capsule, and the second end of the blade of said cutting element is brought into contact with the wall of the capsule and moved in a predetermined circular path, the first end of the blade will follow in said path around the capsule wall to cut a circular opening in said capsule wall.

6. The instrument as described in claim 5 wherein the angle made by the second end of the blade in relation to a horizontal plane passed through said support plate as the blade arches downwardly toward the peak of the blade arch, is less than the angle made by the first end of the blade relative to said plane, as said first end arches downwardly to the peak of the arch.

7. The instrument as described in claim 5 wherein the angle made by the second end of the blade in relation to a horizontal plane passed through said support plate as the blade extends downwardly toward the peak of the blade arch is less than 20 degrees.

8. The instrument as described in claim 5 wherein the angle made by the blade relative to said first leading end of said base portion, as the blade extends downwardly toward the peak of the arch, is less than 20 degrees.

9. An instrument for performing a capsulotomy whereby an opening is cut into the wall of the anterior capsule of a human eye, said instrument comprising:

a probe, said probe being formed as a thin rigid elongated element having a first base end and a second extending end, said first base end being adapted for coupling to the handle means and said probe being transversely orificed perpendicularly to its axis, and inwardly of, but adjacent to, the second extending end of the probe;

an axle rotatably mounted on the second end of said element through said transverse orifice and co-axially with said orifice, said axle having a first end and a second end, said axle first end being secured against withdrawal through the orifice, and said second axle end projecting from said orifice, a rotatable cutter element, said cutter element comprising a thin, downwardly projecting rigid arcuate sharp blade, said blade having a base portion with a first leading end and a second trailing end, and a cutting edge section, said blade cutting edge section being convexly curved away from said base portion between said first and second ends of said base portion for a full extent thereof, and said base portion being secured to the second projecting end of said axle along a portion of said base portion closer to the first leading end of the blade than to its second trailing end, whereby the blade is eccentrically mounted so that, upon application of the leading edge of the blade to a surface to be cut in a predetermined path, the blade rotates about an axis of the axle to cause the remainder of the blade, and particularly its trailing end, to follow said predetermined path.

10. The method of performing a capsulotomy, said method comprising the steps of:

A) making a small incision in the eye;

B) providing a cutting instrument for insertion in said incision to be brought into contact with the anterior wall of the eye capsule, said instrument comprising:

(i) a thin rigid hollow probe having a closed leading end, said closed leading probe end being transversely orificed and supporting an axle rotatable within said orificed end, said axle having a first end secured against withdrawal through said orifice and a second end projecting oppositely through said orifice, said second end supporting an arcuate blade;

(ii) said blade being elongated and having a leading edge and a trailing edge on opposing ends thereof and a cutting edge section, and further having a transversely directed base secured to the second end of the axle, said cutting edge section being arched convexly away from said base between the leading and trailing edges of said blade for a full extend thereof, said base being secured to the second end of the axle more proximately to the leading edge than to the trailing edge of the blade;

C) inserting the blade by its leading edge in a substantially straight path into the incision with the remainder of the blade including its trailing edge following in said path and applying said leading edge to the anterior wall of the capsule in a circular path, whereupon the blade swivels about an axis of the axle to follow said circular path and effect the cutting of a circular opening in said anterior wall; and D) withdrawing said blade from the incision by its leading edge in a straight path, whereby the remainder of the blade including its trailing edge swivels about the axle axis to cause the remainder of the blade, to follow in said straight path without further enlargement of the incision.

11. The method of performing a capsulotomy as described in claim 10 wherein said rigid hollow probe is provided with an opening adjacent its closed leading end and an irrigating fluid is passed through the hollow probe and controllably discharged through the last said opening during the steps of inserting the blade in the incision effecting the circular cutting in the anterior wall and withdrawing the blade through the incision.

12. An instrument for performing a capsulotomy whereby an opening is cut into the wall of the anterior capsule of a human eye, said instrument comprising:

a handle means;

a probe, said probe being formed as a thin rigid elongated tubular element having a first base end and a second end, said first base end being adapted for coupling to the handle means and said second end of the probe being transversely orificed perpendicularly to its axis, and inwardly of, but adjacent to, the second end of the probe;

an axle rotatably mounted on the second end of said element through said transverse orifice and co-axially with said orifice, said axle having a first end and a second end, said first end being secured against withdrawal through the orifice, and said second axle and projecting from said orifice, and said second axle end projecting from said orifice, a cutter element, said cutter element comprising a thin, downwardly projecting rigid arcuate sharp blade, said blade having a widened base portion, a cutting edge section, a first leading end of said base portion and a second trailing end of said base portion, said blade cutting edge section being convexly curved away from said base portion between said first and second ends thereof to form a downwardly projecting arch-shaped cutting edge section disposed below all areas of said base portion, and said widened base portion being secured to the second projecting end of said axle at a point on said base portion closer to its first leading end than to its second trailing end, whereby the cutter element is eccentrically mounted so that, upon application of the leading end of the base portion and its blade to a surface to be cut in a predetermined path, the cutter element will rotate about an axis of the axle to cause the trailing end of the base portion and its blade to follow said predetermined path.

13. The instrument as described in claim 12, wherein the tubular element is hollow from its first base to its second end to enable irrigating fluid to be passed through the probe and out of the second end of its tubular element.

14. The instrument as described in claim 12 wherein the axle of the arcuate curve of the blade of the cutter element is disposed closer to the trailing end of the widened base portion than to the leading end of said base portion.

15. The instrument as described in claim 12 wherein the axle and the base portion and blade of the cutter element are formed as a single integral piece.

16. The instrument as described in claim 12 wherein the angle made by the blade relative to said first leading end of said base portion, as the blade extends downwardly toward the peak of the blade arch is less than the angle made by the blade relative to the second trailing end of said base portion.

17. The method of performing a capsulotomy, said method comprising the steps of:
   A) making a small incision in the eye;
   B) providing a cutting instrument for insertion in said incision to be brought into contact with the anterior wall of the eye capsule, said instrument comprising:
      (i) a thin, rigid tubular probe having a leading end, said leading end being transversely orificed and supporting an axle rotatable within said orificed end, said axle having a first end secured against withdrawal through said orifice and a second end projecting oppositely through said orifice;
      (ii) a cutter element supported by said second end of the axle, said cutter element comprising a narrow elongated blade having (1) a base portion secured to the second end of the axle, (2) a leading edge disposed at one end of said base portion, (3) a trailing edge disposed at an opposing end of said base portion, and (4) an arcuate cutting edge extending convexly downwardly from said base portion between the leading and trailing edges thereof below all areas of said base portion, said base portion extending transversely to an axis of the axle, said base portion between the leading and trailing edges thereof below all areas of said base portion, said base portion extending transversely to an axis of the axle, said base portion being secured to the second end of the axle more proximately to the leading edge than to the trailing edge of the blade;
   C) inserting the blade by its leading edge in a substantially straight path into the incision with the remainder of the blade including its trailing edge following in said path;
   D) applying said leading edge of the blade to cut the anterior capsule wall in a circular path, whereupon the cutter element swivels about the axis of the axle to cause the trailing edge of the blade to follow said circular path and effect the cutting of a circular opening in said anterior wall; and
   E) withdrawing said blade from the incision by its leading edge in a straight path, whereby the remainder of the blade, including its trailing edge, swivels about the axle axis to cause the remainder of the blade, to follow in said straight path without further enlargement of the incision.

18. The method of performing a capsulotomy as described in claim 17 wherein said rigid hollow probe is provided with an opening at its leading end and an irrigating fluid is passed through the hollow probe and controllably discharged through the last said opening during the steps of inserting the blade in the incision, effecting the circular cutting in the anterior wall and withdrawing the blade through the incision.

* * * * *